(12) United States Patent
Curry (10) Patent No.: US 11,478,368 B1
(45) Date of Patent: Oct. 25, 2022

(54) DEVICE AND METHOD FOR CLEANING A PROSTHETIC LINER

(71) Applicant: Richard Curry, Spring Grove, PA (US)

(72) Inventor: Richard Curry, Spring Grove, PA (US)

( * ) Notice: Subject to any disclaimer, the term of this patent is extended or adjusted under 35 U.S.C. 154(b) by 0 days.

(21) Appl. No.: 17/363,275

(22) Filed: Jun. 30, 2021

(51) Int. Cl.
*A61F 2/78* (2006.01)
*B08B 13/00* (2006.01)
*B08B 11/02* (2006.01)
*A61F 2/50* (2006.01)

(52) U.S. Cl.
CPC ............ *A61F 2/7812* (2013.01); *B08B 11/02* (2013.01); *B08B 13/00* (2013.01); *A61F 2002/5081* (2013.01); *A61F 2002/7818* (2013.01); *A61F 2002/7875* (2013.01)

(58) Field of Classification Search
CPC .. A61F 2/78; A61F 2/7812; A61F 2002/5081; A61F 2002/7818; A61F 2002/7875
See application file for complete search history.

(56) References Cited

U.S. PATENT DOCUMENTS

| | | | |
|---|---|---|---|
| 5,376,129 A * | 12/1994 | Faulkner | B29C 61/06 623/32 |
| 7,775,365 B1 * | 8/2010 | More | A61F 2/76 206/572 |
| 8,808,394 B2 | 8/2014 | Laghi | |
| 2022/0015561 A1 * | 1/2022 | Rodenbostel | F16B 45/00 |

OTHER PUBLICATIONS

WillowWood, Patient Instructions, The Ohio Willow Wood Company, Jan. 21, 2015, 2 pages (Year: 2015).*
Ottobock. How to clean my liner? YouTube, Jan. 4, 2019, 5 screen shots captured on Jun. 8, 2022, youtube.com/watch?v=czstCBXLPoo (Year: 2019).*

* cited by examiner

*Primary Examiner* — Bruce E Snow
(74) *Attorney, Agent, or Firm* — Hooker & Habib, P.C.

(57) ABSTRACT

A method for supporting a pin-type prosthetic liner includes placing the liner in an inverted state on a standoff extending from the base of a liner stand. The standoff extends to an upper end that supports the liner on the liner stand. The upper end is an open end that receives the pin of the inverted liner being supported on the liner stand.

14 Claims, 7 Drawing Sheets

DEVICE AND METHOD FOR CLEANING A PROSTHETIC LINER

FIELD OF THE DISCLOSURE

The disclosure relates generally to a device and method for cleaning an object, and in particular, to cleaning polymeric prosthetic liners used by amputees.

BACKGROUND OF THE DISCLOSURE

Polymeric prosthetic liners ("liners" herein) are used by amputees to secure a prosthesis to a residual limb of an arm or leg. Liners are typically formed using various polymeric materials, including, for example, silicone, urethane, and thermoplastic elastomer (TPE) gels.

Figure 9:
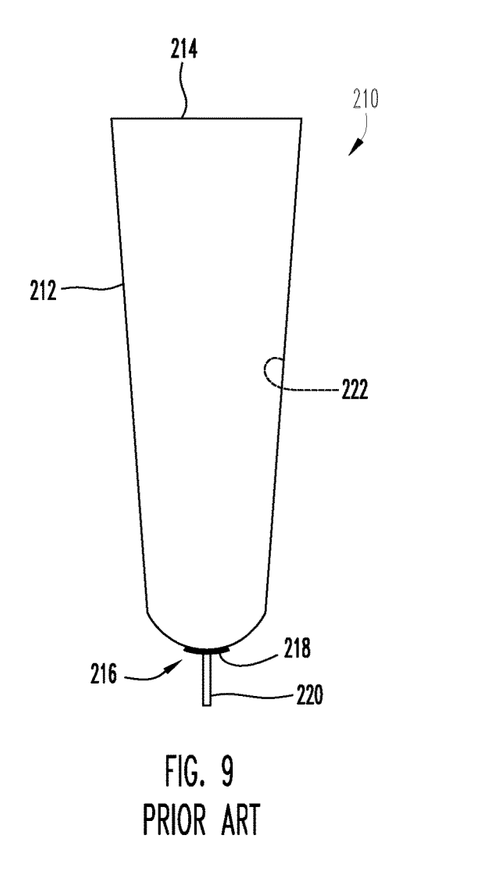
FIG. 9 is a side view of a prior art pin-type prosthetic liner in its non-inverted state.

FIG. 9 illustrates a conventional pin-type liner 210 used to secure a prosthetic foot (not shown) to the residual limb of a lower limb amputee. The liner includes a generally tubular body 212 formed of a polymeric material. The liner may also include an interior fabric liner (not shown).

The body 212 has an open end 214 forming an open end of the liner 210 that receives the residual limb. The body 212 extends longitudinally to a closed body end 216 disposed at a closed end portion of the liner 210. A buttress 218 is also disposed at the closed end portion of the liner 210. The buttress 218 is generally disc-shaped but has curved inner and outer surfaces that conform to the general curvature of the closed liner body end 216. The buttress 218 is typically stiffer than the body material and may, for example, be made of glass-reinforced nylon, metal, rigid plastic, or the like. The illustrated liner 210 is secured to the prosthetic foot by an elongate pin 220 fastened to the buttress 218 and extending away from the lower end of the body.

An example of a pin-type liner that can be used with the disclosed method is disclosed in Laghi U.S. Pat. No. 8,808, 394, which is incorporated by reference as if fully set forth herein.

To use the liner 210, the user rolls the liner 210 onto the residual limb. The inner surface 222 of the liner body 212 is against the user's skin. The residual limb is inserted into the socket of the prosthetic foot, inserting the pin 212 into the foot's locking mechanism. The pin 220 typically includes serrations or the like (not shown) that cooperate with the locking mechanism to secure the prosthetic foot against the buttress 218. The buttress 218 is disposed between the prosthetic foot and the residual limb in use and helps support the pin 220 and the lower limb against the prosthetic foot.

Figure 10:
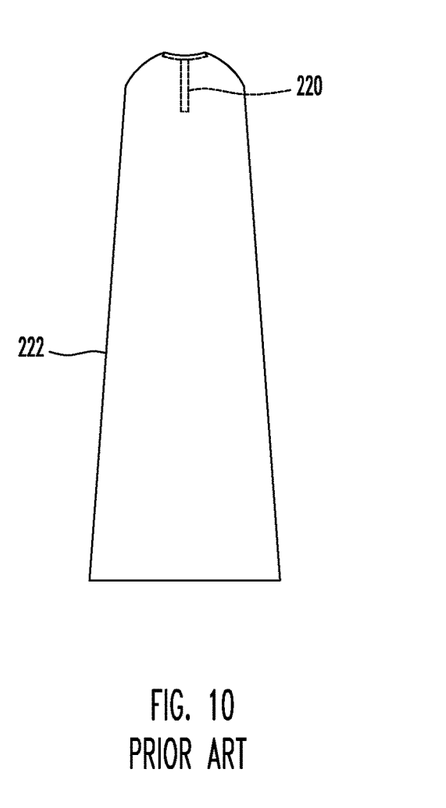
FIG. 10 is similar to FIG. 7 but showing the pin-type prosthetic liner in its inverted state.

After use, the user unlocks the prosthetic foot from the pin 212 and removes the foot. The user then unrolls the liner 210 off the residual limb. The unrolled liner 210 typically comes off the limb in an "inside out" or inverted state as shown in FIG. 10. That is, the surface 222 of the liner body 212 is now an outer surface of the inverted liner as shown in FIG. 10. The pin 220 is now disposed inside of the liner 220 and extends into the interior of the inverted liner.

During use of the liner 210, perspiration, dirt, oil, bacteria, etc. builds up on the inner surface 222 of the liner. It is recommended that the inner surface 222 of the liner be manually cleaned with water and a compatible cleaner (such as soap, detergent, or a specially formulated cleanser compatible with the liner material) after each use. Washing the liner in a sink or bathtub can be difficult because the liner can be slippery and difficult to handle.

After washing, the liner 210 may be supported on a liner dryer stand until both the inside and outside of the liner are dry. A liner dryer stand includes a support base and an elongate standoff that extends away from the base to a closed upper end. The liner in the normal non-inverted state as shown in FIG. 9 is placed over the standoff. The closed upper end of the standoff is designed to sufficiently conform to the shape of the buttress 218 and thereby provide stable support of the liner that spaces the liner away from the support base during drying.

An inverted liner 210 as shown in FIG. 10 may be placed on the liner dryer stand to support the liner and exposing the normally inner liner surface 222 for manual cleaning with both hands. However, interference between the closed upper end of the liner dryer stand and the pin 220 spaces the buttress 218 away from the standoff. The inverted liner 210 is not well supported on the liner stand, making washing the liner difficult.

Cleaning a non-inverted hanger placed on the liner stand or hanging from a modified clothes hanger that supports the liner from the pin 220 is also difficult because the surface 222 to be cleaned is now inside the liner 210.

Thus there is a need for a better method for cleaning the inner surface 222 of a pin-type liner after use. The method should enable cleaning an exposed liner inner surface with both hands while the liner is being reliably supported.

SUMMARY OF THE DISCLOSURE

Disclosed is a method for cleaning the exposed inner surface of a pin-type liner after use. The disclosed method enables cleaning the liner inner surface with both hands while the liner is being reliably supported. Further, the disclosed method utilizes a liner stand that can also support the pin-type liner while drying or for normal storage when the liner is not in use.

The disclosed method includes the step of providing a liner stand having a base and an elongate standoff extending away from the base to an open upper end of the standoff. The open upper end of the standoff receives the pin of a pin-type liner into the standoff and enabling the buttress of the liner to be supported against the upper end of the standoff.

An embodiment of the disclosed liner stand includes two spaced apart standoffs, enabling multiple liners to be washed at the same time.

A further embodiment of the liner stand has each standoff of the liner stand being removably fastenable to the base for easier transport of the liner stand.

Other objects and features of the disclosure will become apparent as the description proceeds, especially when taken in conjunction with the accompanying drawing sheets illustrating one or more illustrative embodiments.

DETAILED DESCRIPTION

Figure 1:
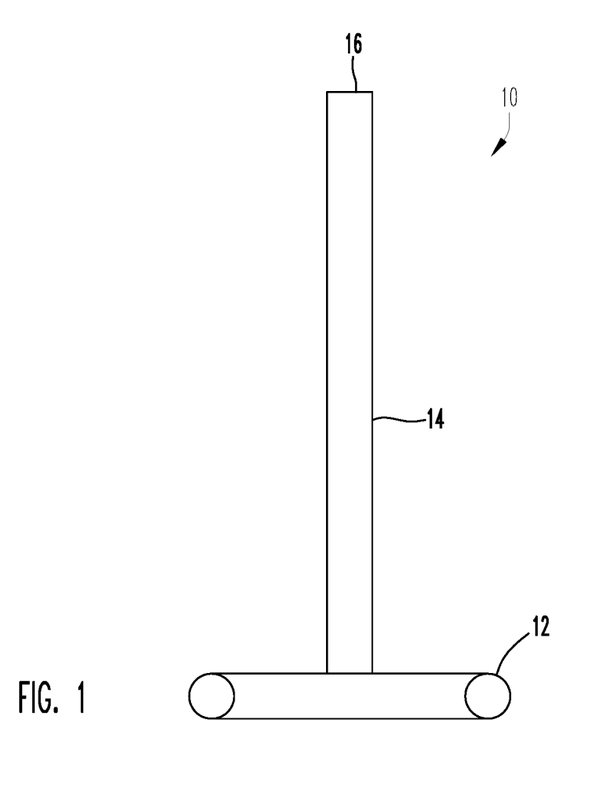
FIGS. 1 and 2 are side and top views of a first embodiment liner stand for practicing the disclosed method for washing.
Figure 2:
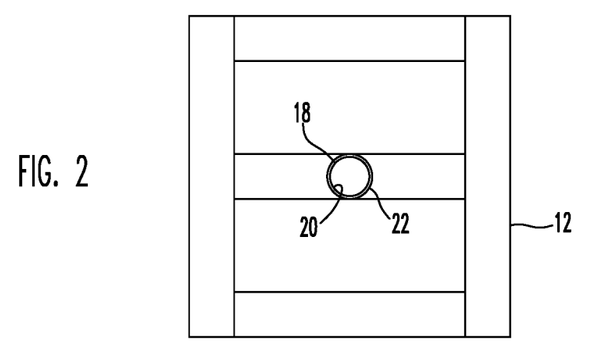

FIGS. 1 and 2 illustrate a liner stand 10 in accordance with this disclosure. The liner stand 10 can be used to support a liner for washing, washing and drying, drying, or storage when the liner is not in use.

The liner stand 10 includes a base 12 and an elongate standoff 14 attached to the base 12. The base 12 is configured to stably support a liner placed on the standoff 14. The standoff extends vertically from the base to an upper end 16. The illustrated standoff 14 is formed as a tubular member whereby the upper end 16 is an open end of the standoff. The upper end defines a flat, annular horizontal surface 18 bounded by a circular interior wall 20 and a circular exterior wall 22 of the standoff 14.

Figure 3:
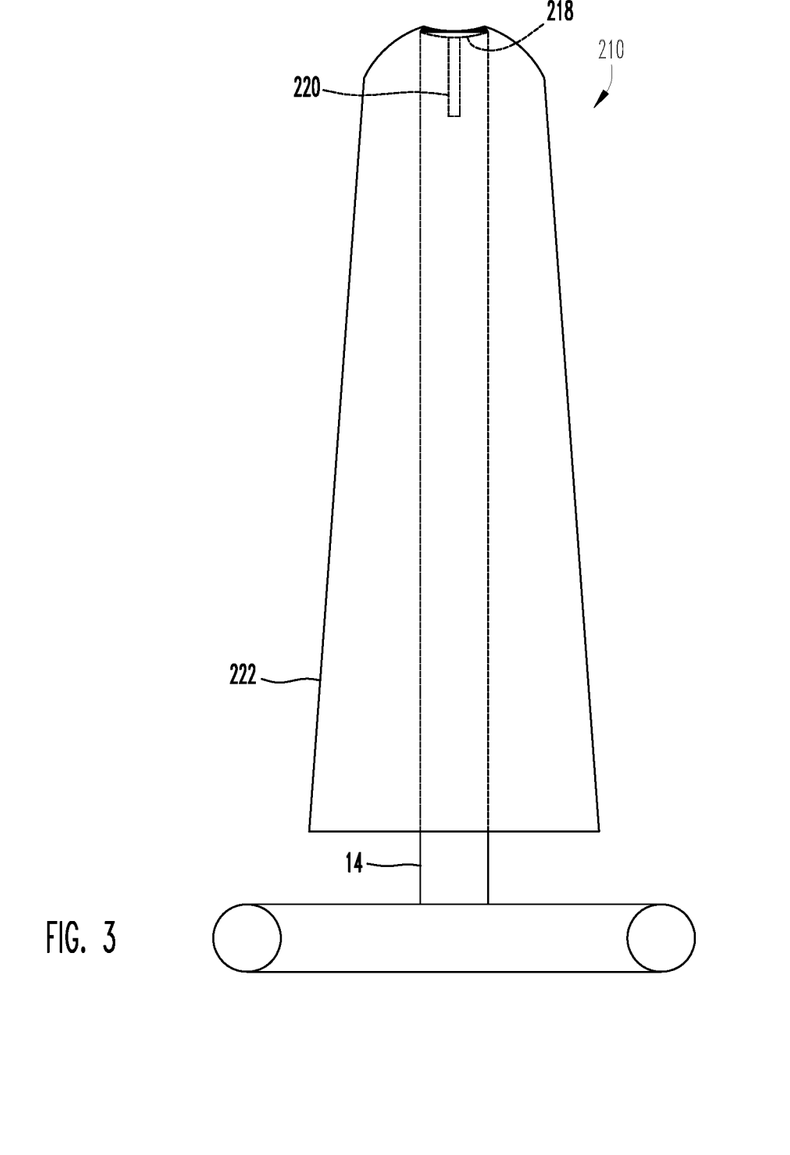
FIG. 3 is similar to FIG. 1 but includes an inverted pin-type liner placed on the liner stand for washing.

FIG. 3 illustrates an inverted liner 210 placed on the standoff 14. The liner buttress 218 is supported on the upper end 16 of the standoff 14 and with the liner pin 220 extending from the buttress 218 into the standoff 14. The curved outer surface of the buttress 218 also extends into the standoff 14 and is supported by the upper horizontal surface 18 of the standoff 14. The diameter of the interior wall 20 is selected such that the upper end of the standoff 14 reliably and stably supports the buttress 218 and the entire liner 210 on its upper end.

The standoff 14 spaces away the liner 210 from the base 12 and supports the liner 210 for washing with the liner surface 222 facing outwardly and accessible for easy cleaning of the liner surface 222 by use of both hands or other cleaning tools.

After washing, the liner 210 can remain on the liner stand 10 for drying, with the liner inside surface 222 still disposed on the outside of the inverted liner 210.

Figure 4:
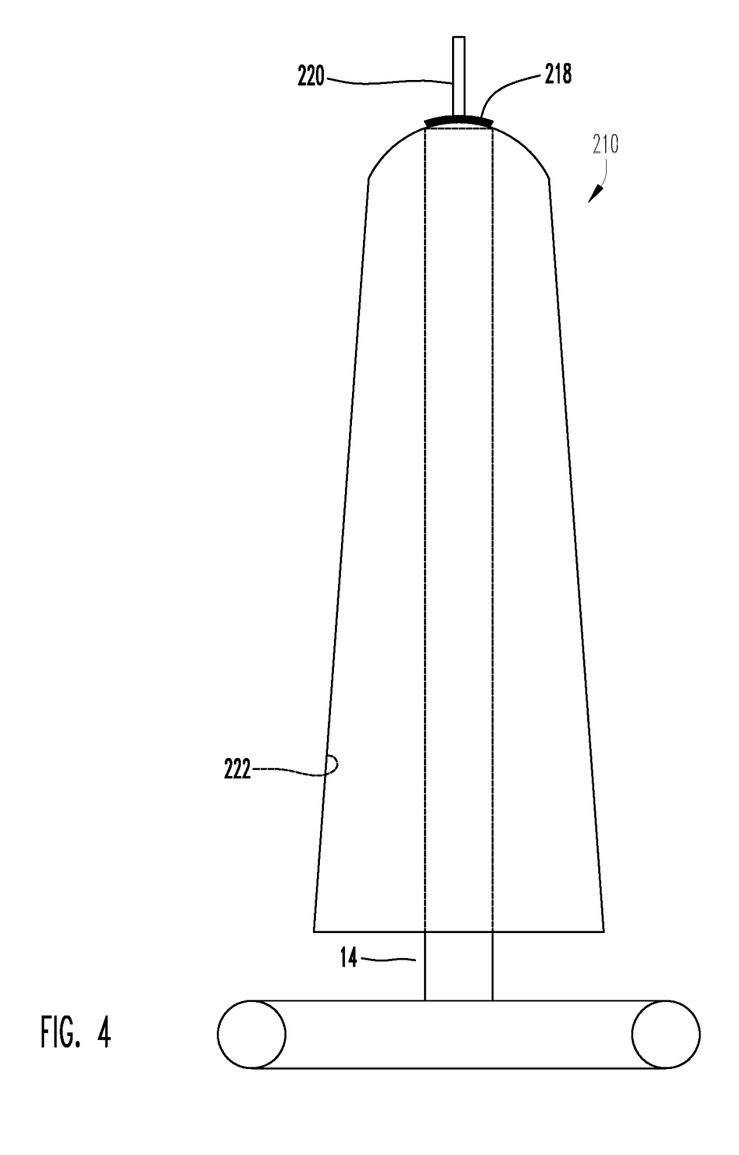
FIGS. 4 and 5 are side and top views of a second embodiment liner stand for practicing the disclosed method for washing.

The liner stand 10 may also be used as a regular stand for storing an unused liner 210. FIG. 4 illustrates a non-inverted liner 210 supported on the standoff 14. The curved surface of the liner buttress 218 is supported on the top surface of the standoff 14. In possible embodiments the standoff 14 is sized such that the liner buttress 218 can extend beyond the standoff 14. The liner stand 10 is thus suitable for both washing an inverted liner, storing a non-inverted liner, and washing the outside of a non-inverted liner.

Figure 5:
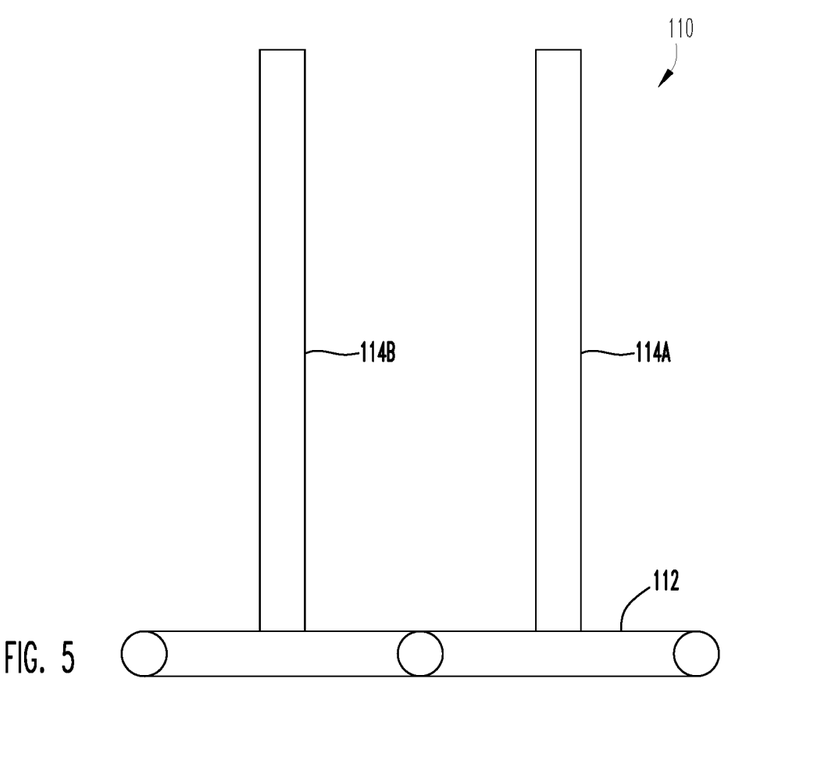
Figure 6:
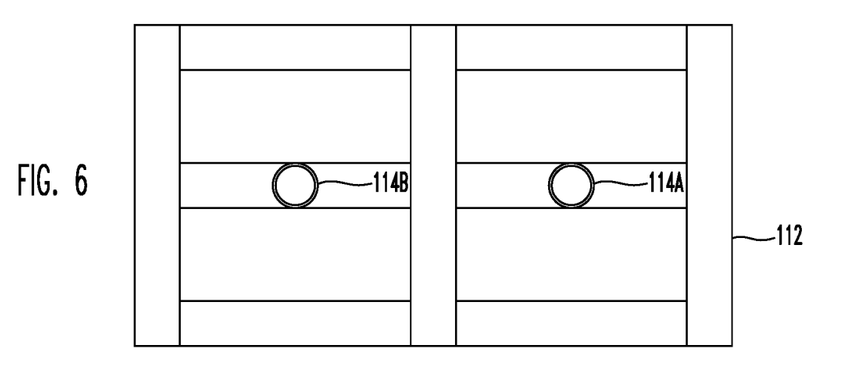
FIG. 6 illustrates the steps of the disclosed method for washing.

FIGS. 5 and 6 illustrate a second embodiment liner stand 110. The liner stand 110 includes a base 112 that supports a pair of spaced-apart standoffs 114A, 114B, the standoffs 114A, 114B being identical to the standoff 14. The liner standoffs are spaced a sufficient distance apart to allow simultaneous washing/drying/storage of two liners 210.

Figure 7:
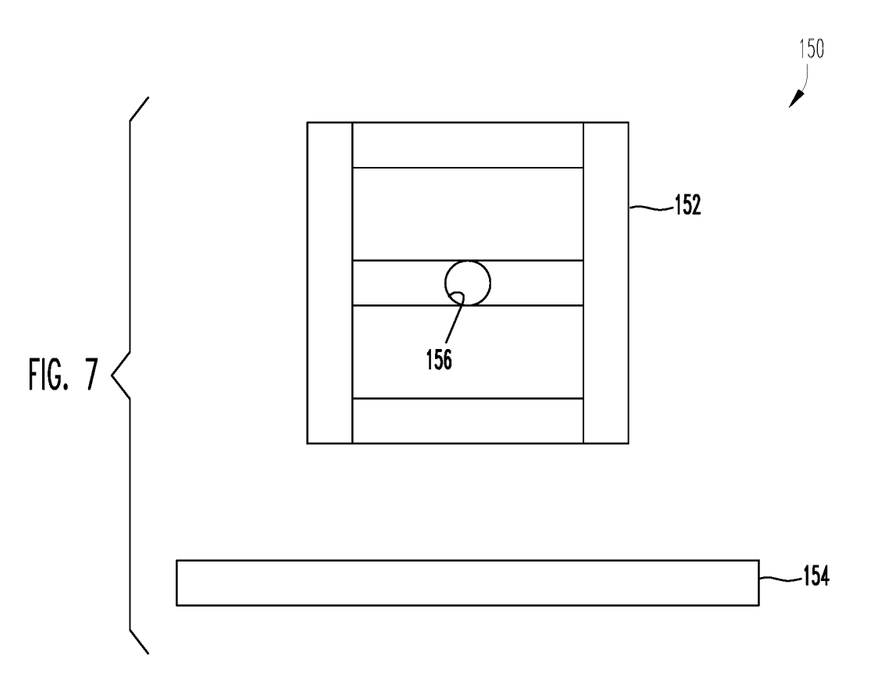
FIG. 7 illustrates a kit for forming a third-embodiment liner stand for practicing the disclosed method for washing.

FIG. 7 illustrates a third embodiment liner stand 150 that is provided as a kit having a base 152 and a separate standoff 154. The standoff 154 is removably fastenable to the base 152 by, in the illustrated embodiment, a threaded connection formed by a threaded lower end of the standoff 154 being threaded into a threaded hole 156 in the base 152. The assembled kit forms a liner stand similar to the liner stand 10.

Figure 8:
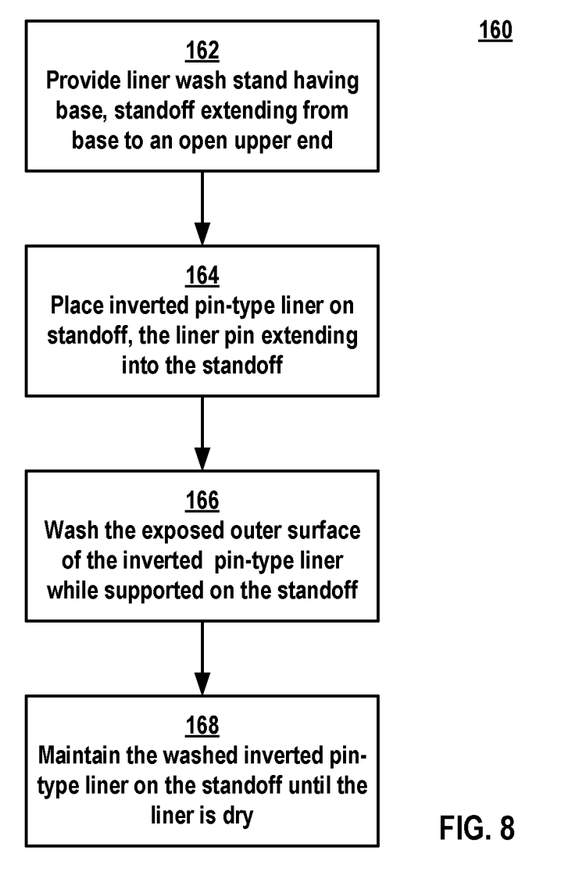
FIG. 8 is a flow chart illustrating the steps of washing a pin-type liner in accordance with this disclosure.

FIG. 8 illustrates the steps 160 of washing a pin-type liner in accordance with this disclosure. In step 162, a liner stand having a base and standoff having an open upper end is provided as previously described. The inverted liner is placed on the standoff and supported on the upper end of the standoff, the pin extending into the standoff, step 164. The outer surface of the inverted liner is then washed, step 166. The washed liner can remain on the standoff until dry, step 168.

The illustrated liner stands 10, 110, 150 are constructed from lengths of PVC tubing and PCV tubing pipe fittings available at any home improvement store. In other embodiments liner the stand 10 can be made from other materials to meet different design goals such as lighter weight, desired appearance, manufacturing costs, etc. The shape and design of the bases 12, 112 and the shape, length, and design of the standoffs 14, 114 could also vary from what is shown to accommodate different sized liners or liner buttresses.

While this disclosure includes one or more illustrative embodiments described in detail, it is understood that the one or more embodiments are each capable of modification and that the scope of this disclosure is not limited to the precise details set forth herein but include such modifications that would be obvious to a person of ordinary skill in the relevant art including (but not limited to) changes in material selection, size, operating ranges (contact member travel, lost motion, and the like), environment of use, number and arrangement of contact pads, monolithic versus modular backplane construction, and the like, as well as such changes and alterations that fall within the purview of the following claims.

What is claimed is:

1. A method for supporting a pin-type prosthetic liner for washing, drying, or storage of the liner, the liner of the type used by an amputee to secure a prosthesis to a residual limb and comprising a tubular body extending from an open end to a closed end and an elongate pin extending away from the closed end of the body wherein the liner in a non-inverted state receives a residual limb of an amputee to secure a prosthesis to the residual limb, the method comprising the steps of:
    (a) providing a liner stand, the liner stand comprising a base and an elongate standoff extending away from the base to an upper end of the standoff, the upper end of the standoff being an open end of the standoff; and
    (b) placing the liner on the standoff, the standoff being received into the liner body through the open end of the liner body.

2. The method for supporting a pin-type liner of claim 1 wherein step (b) comprises the steps of:
    (c) placing the liner in an inverted state on the standoff and receiving the pin of the liner into the open end of the liner body.

3. The method for supporting a pin-type liner of claim 2 further comprising the step of:
    (d) washing an exposed outer surface of the liner while the liner is on the standoff.

4. The method for supporting a pin-type liner of claim 3 further comprising the step of:
    (e) after performing step (d), leaving the washed liner on the liner stand until the washed outer surface is dry.

5. The method for supporting a pin-type liner of claim 1 wherein the liner comprises a buttress disposed at the closed end of the liner body, the pin extending from the buttress, wherein step (b) further comprises the step of:
    (d) supporting the liner buttress on the upper end of the standoff after performing step (b).

6. The method for supporting a pin-type liner of claim 1 wherein the liner is wet while performing step (a) and further comprising the step of:
    (c) leaving the wet liner on the liner stand until the wet liner becomes dry.

7. A liner stand in combination with a pin-type prosthetic liner of the type used by an amputee to secure a prosthesis to a residual limb, the liner comprising a tubular body extending from an open end to a closed end being disposed at a closed end portion of the liner and an elongate pin extending away from the closed end portion of the body wherein the liner in a non-inverted state receives a residual limb of an amputee to secure a prosthesis to the residual limb, the combination comprising:

- a liner stand comprising a base and an elongate standoff extending away from the base to an upper end of the standoff, the upper end of the standoff being an open end of the standoff;
- a pin-type prosthetic liner comprising a tubular body and an elongate pin, the liner body extending from an open end to a closed end, the closed end of the body being disposed at a closed end portion of the liner, the pin extending away from the closed end of the body;
- the liner being supported on the liner stand, the liner being supported on the upper end of the standoff with the liner being in an inverted state and the pin being received into the open upper end of the standoff whereby the closed end portion of the liner is supported against the upper end of the standoff.

8. The combination of claim 7 wherein the liner comprises a buttress disposed at the closed end portion of the liner body, the pin extending from the buttress, the buttress being supported against the upper end of the standoff.

9. The combination of claim 7 comprising a cleanser applied to an exposed outer surface of the liner.

10. The combination of claim 7 comprising a wet liner being supported on the liner stand.

11. The combination of claim 7 wherein the standoff is a first standoff of the liner stand, the liner stand comprising at least one additional standoff extending from the base, each additional standoff being like the first standoff.

12. The combination of claim 7 wherein the base is made of plastic.

13. The combination of claim 12 wherein the standoff is made of plastic.

14. The combination of claim 7 wherein the standoff is removably fastenable to the base whereby the standoff can be separated from the base for transport of the liner stand.

* * * * *